United States Patent
Zibold et al.

(10) Patent No.: US 9,304,107 B2
(45) Date of Patent: Apr. 5, 2016

(54) DETECTION OF A METAL OR MAGNETIC OBJECT

(75) Inventors: Tobias Zibold, Stuttgart (DE); Andrej Albrecht, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 689 days.

(21) Appl. No.: 13/696,363

(22) PCT Filed: Mar. 8, 2011

(86) PCT No.: PCT/EP2011/053451
§ 371 (c)(1),
(2), (4) Date: Feb. 15, 2013

(87) PCT Pub. No.: WO2011/138063
PCT Pub. Date: Nov. 10, 2011

(65) Prior Publication Data
US 2013/0134968 A1    May 30, 2013

(30) Foreign Application Priority Data

May 7, 2010   (DE) .................. 10 2010 028 723

(51) Int. Cl.
*G01N 27/72* (2006.01)
*G01V 3/10* (2006.01)

(52) U.S. Cl.
CPC .............. *G01N 27/72* (2013.01); *G01V 3/104* (2013.01)

(58) Field of Classification Search
CPC ..................................................... G01N 27/72
USPC .......................................................... 324/232
See application file for complete search history.

(56) References Cited

U.S. PATENT DOCUMENTS 5,952,822 A    9/1999   Kayserman et al.

FOREIGN PATENT DOCUMENTS

| | | |
|---|---|---|
| CN | 100337127 C | 9/2007 |
| DE | 41 41 264 C1 | 3/1993 |
| DE | 10 2004 047 189 A1 | 4/2006 |
| DE | 10 2007 053 881 A1 | 5/2009 |
| WO | 95/00818 A1 | 1/1995 |

OTHER PUBLICATIONS

Werner Turck, Partial Translation of DE4141264, Mar. 18, 1993.*
International Search Report corresponding to PCT Application No. PCT/EP2011/053451, mailed Aug. 8, 2012 (German and English language document) (6 pages).

* cited by examiner

*Primary Examiner* — Bot Ledynh
(74) *Attorney, Agent, or Firm* — Maginot, Moore & Beck LLP

(57) ABSTRACT

A measuring device configured to detect a metal object includes two emission coils configured to produce superimposed magnetic fields. The measuring device also includes a device configured to determine a differential voltage between the emission coils. The measuring device further includes a control device configured to supply the emission coils with alternating voltages such that the value of an AC voltage component of the differential voltage, which is time synchronized with the alternating voltage, is minimized. The control device is configured to detect the metal object when the ratio of the alternating voltages does not correspond to the ratio of the impedances of the emission coils when the metal object is not there.

10 Claims, 3 Drawing Sheets

DETECTION OF A METAL OR MAGNETIC OBJECT

This application is a 35 U.S.C. §371 National Stage Application of PCT/EP2011/053451, filed on Mar. 8, 2011, which claims the benefit of priority to Serial No. DE 10 2010 028 723.7, filed on May 7, 2010 in Germany, the disclosures of which are incorporated herein by reference in their entirety.

Certain work on workpieces presents the risk of an article concealed in the workpiece being damaged by the work. By way of example, when drilling into a wall, a water, power or gas line running inside the wall can be damaged. Conversely, it may be desirable to perform the work specifically such that an article concealed in the workpiece is worked on at the same time, for example if the hole from the above example is intended to pass through a steel reinforcement or a supporting structure inside the wall.

BACKGROUND

For the purpose of sensing such a concealed article, coil-based metal detectors are known in the prior art. Such detectors produce a magnetic field in a measurement region. If there is a metallic article in the measurement region, the article is recognized on the basis of its influence on the magnetic field produced. Frequently, the magnetic field produced is determined by using at least two reception coils which are oriented and connected to one another such that in the absence of a metallic object in the measurement region the measurement signal delivered by both reception coils together is virtually zero (differential measurement). In one variant, a plurality of transmission coils are used to produce the magnetic field, said transmission coils being activated such that the signal measured in the two reception coils is virtually zero regardless of any absence of a metallic object in the measurement region (field-compensated measurement).

DE 10 2007 053 881 A1 describes a measurement method for determining the position or the angle of a coil relative to two further coils. To this end, two transmission coils arranged at an angle relative to one another are used to generate a magnetic alternating field. A reception coil is put into the magnetic alternating field and the actuation of the transmission coils is altered such that the same voltage is induced in the reception coil by each of the transmission coils. A ratio of current values supplied to the transmission coils serves as a measure of determination of the position and/or angle of the reception coil relative to the transmission coils.

DE 10 2004 047 189 A1 describes a metal detector having printed coils.

The disclosure is based on the object of providing simple precise detection for a metallic object. A further object of the disclosure is to specify a method for determining the metallic object.

SUMMARY

The disclosure achieves these objects by means of a measuring apparatus having the features described below and a method having the features described below. Description below specifies preferred embodiments.

According to the disclosure, a measuring apparatus for sensing a metallic object comprises two transmission coils for producing overlaid magnetic fields and a device for determining a differential voltage applied between the transmission coils. In addition, a control device is provided in order to supply the transmission coils with alternating voltages such that an AC voltage component of the differential voltage, which AC voltage component is in sync with the alternating voltages, is minimized in terms of absolute value. The control device is set up to sense the object when the ratio of the alternating voltages does not correspond to the ratio of impedances of the transmission coils in the absence of the metallic object.

This is the case when the impedances of the transmission coils are influenced by the metallic object in different ways on the basis of different distances. By dispensing with a receiver coil or a magnetic sensor in the region of the transmission coils, it is possible to reduce the number of coils for the measuring apparatus, which allows the space required for the measuring apparatus to be reduced and manufacturing costs to be saved. The compact design which is thus possible allows a large number of measuring apparatuses to be arranged on a small space, which means that it is possible to increase a spatial resolution of measured values to enter a range that can be presented.

Preferably, the alternating voltages are AC voltages, in order to change the magnetic fields of the transmission coils periodically in terms of absolute value and phase. The AC voltages allow synchronous demodulation, which can be used to very effectively reject interfering signals at frequencies that are not equal to the modulation frequency. Furthermore, the AC voltages can produce alternating magnetic fields, in order to induce eddy currents in nonmagnetic materials, such as copper, on the basis of which said materials can then be detected.

Preferably, the device for determining the differential voltage is formed from two series-connected nonreactive resistors which are each part of the complex resistance of one of the transmission coils. Discrete resistors can thus be dispensed with, which allows manufacturing costs to be reduced.

The transmission coils may be arranged in two spaced, parallel planes, such that the magnetic fields therefrom are oriented parallel. It is then possible to recognize a position of the metallic object relative to the planes from which transmission coil is being supplied with a voltage that is magnified in comparison with the object-free case. Metallic objects which are situated on the other side of the plane of one of the transmission coils can be ignored, in order to avoid a false measurement which is caused by a user of the measuring apparatus, for example.

One or both of the transmission coils may be air-core coils and may be in the form of printed coils, particularly in the form of a printed circuit on a circuit board. This allows the measuring device to be designed such that it reacts only very slightly to temperature or ageing influences, which allows calibration to be effected once in the course of manufacture of the measuring apparatus. By virtue of the transmission coils being in the form of printed coils on the circuit board, it is possible for the transmission coils to be produced precisely with little production complexity. In this case, the control device may be designed to be on the same circuit board. By minimizing wiring and component-fitting costs, it is thus possible to save further manufacturing costs.

According to a further aspect of the disclosure, a method for sensing a metallic object comprises the steps of producing magnetic fields in an aligned orientation by means of two transmission coils, supplying the transmission coils with alternating voltages and sensing the object when the ratio of the alternating voltages does not correspond to the ratio of the currents flowing through the transmission coils.

The disclosure may also be implemented as a computer program product, wherein a computer program product according to the disclosure comprises program code means for carrying out the described method and is able to be executed on a processing device or stored on a computer-readable data storage medium.

BRIEF DESCRIPTION OF THE DRAWINGS

The disclosure is described in more detail below with reference to the accompanying figures, in which.

DETAILED DESCRIPTION

Figure 1:
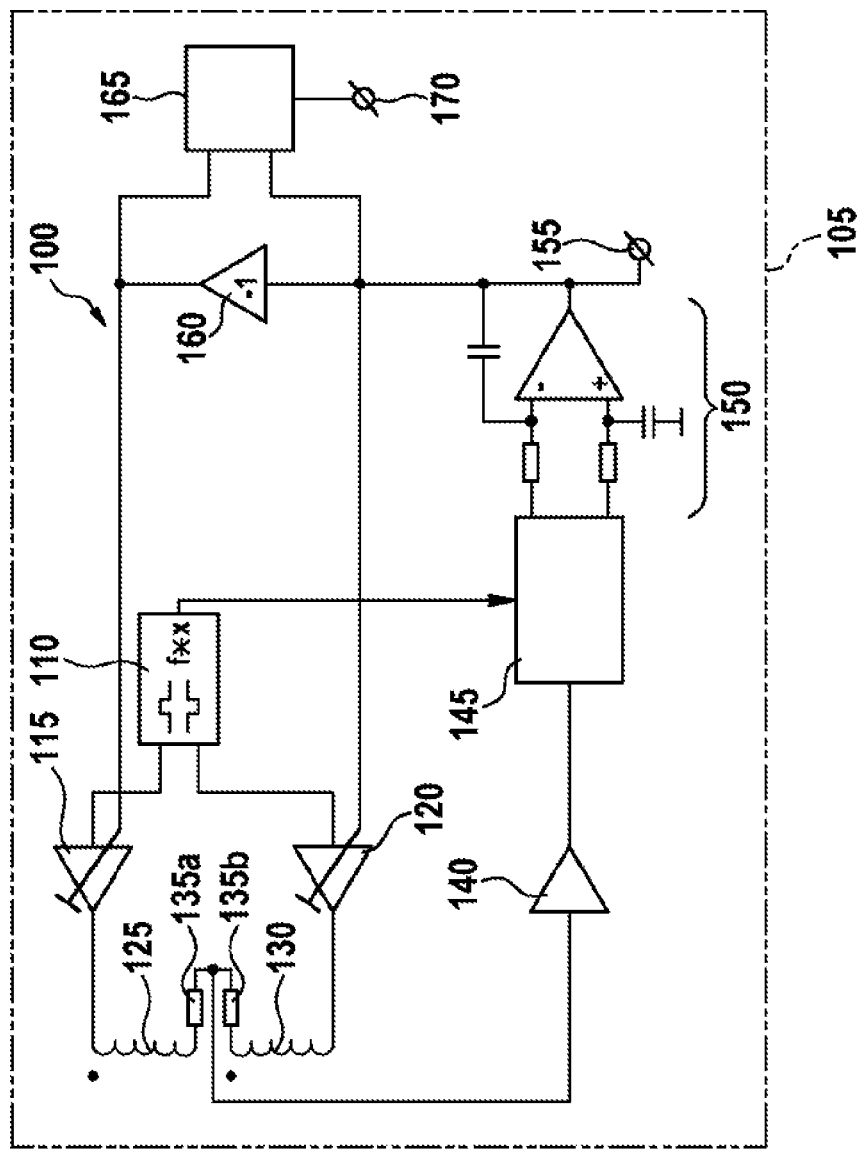
FIG. 1 shows a block diagram of a measuring apparatus.

FIG. 1 shows a block diagram of a measuring apparatus 100. The measuring apparatus 100 is part of a metal detector 105 for sensing metallic objects, for example made of ferrous material.

A clock generator 110 has two outputs at which it provides periodic alternating signals having a phase shift, preferably a 180° phase shift. The alternating signals may comprise square-wave, triangular-waveform or sinusoidal signals, in particular. The outputs of the clock generator are connected to a first controllable amplifier 115 and a second controllable amplifier 120, respectively. Each of the controllable amplifiers 115, 120 has a control input which it uses to receive a signal which controls a gain factor of the controllable amplifier 115, 120. An output of the first controllable amplifier 115 is connected to a first transmission coil 125 and one output of the second controllable amplifier 120 is connected to a second transmission coil 130. The remaining ends of the transmission coils 125 and 130 are connected to one another via a first and a second resistor 135a, 135b, respectively. In one embodiment, the resistors 135a, 135b are formed by the non-reactive resistances of the transmission coils 125 and 135, respectively.

Each of the two transmission coils 125 and 130 carries the same respective current at any time. The polarities and amplitudes of the alternating voltages supplied to the two transmission coils 125, 130 do not have a separate influence on the magnetic fields produced in the coils 125, 130. As indicated in FIG. 1 by the dots on the transmission coils 125, 130, the two transmission coils 125, 130 are oriented in the same sense. Therefore, the transmission coils set up magnetic fields with an orientation in the same direction; although magnetic fields in opposite directions, as are produced by transmission coils wound in opposite senses, are likewise possible, they are generally less advantageous on account of the minute dipole component of the overlaid magnetic field. However, it is conceivable that this disadvantage is consciously utilized when it is desirable to restrict the detection depth.

A connection runs from the interconnected resistors 135a, 135b to an input amplifier 140. The input amplifier 140 is shown with a constant gain factor; in other embodiments, however, a gain factor for the input amplifier 140 may also be controllable. By way of example, this allows a spatial resolution and/or sensitivity of the measuring apparatus 100 to be influenceable and, by way of example, to be controllable on the basis of a measured variable.

The output of the input amplifier 140 is connected to a synchronous demodulator 145. The synchronous demodulator 145 is also connected to the clock generator 110 and receives from the latter a clock signal which indicates the phase of the signals provided at the outputs of the clock generator 110. In a simple embodiment, in which the signals provided by the clock generator 110 are symmetrical square-wave signals, one of the output signals can be used as clock signal. The synchronous demodulator 145 essentially takes the clock signal provided by the clock generator 110 as a basis for connecting the measurement signal received from the input amplifier 140 alternately to its upper or lower output.

The two outputs of the synchronous demodulator 145 are connected to an integrator (integrating comparator) 150, which in this case is shown as an operational amplifier connected up to two resistors and two capacitors. Other embodiments are likewise possible, for example as an active low-pass filter. A digital implementation subsequent to the synchronous demodulator is also conceivable, in the case of which the signal at the output of the synchronous demodulator is subjected to analog-to-digital conversion at one or more time(s) within a half-cycle and is then compared with the corresponding value from the next half-cycle. The difference is integrated and, by way of example, converted back to an analog signal and used for controlling the amplifiers. While the synchronous demodulator 145 provides the measurement signal received from the input amplifier 140 at the lower of its outputs, the integrator 150 integrates this signal over time and provides the result at its output. While the synchronous demodulator 145 provides the measurement signal received from the input amplifier 140 at its upper output, this signal is integrated by the integrator 150 in inverted form over time and the result is provided at the output of the integrator 150. The voltage at the output of the integrator is the integral of the difference between the low-pass-filtered outputs of the synchronous demodulator.

The differential voltage that can be tapped off between the resistors 135a, 135b can be used to sense an impedance difference between the transmission coils 125 and 130. The impedance of each of the transmission coils 125, 130 is dependent on a distance of a metallic object from the transmission coil 125, 130. If the impedances of the transmission coils 125, 130 are of the same magnitude, the signals provided at the outputs of the synchronous demodulator 145 are also of equal magnitude on average over time, and the output of the integrator 150 provides a signal which is virtually zero (ground). If the impedances of the transmission coils 125, 130 differ, however, then the signals provided at the outputs of the synchronous demodulator 145 are no longer equal on average, and the output of the integrator 150 provides a positive or negative signal.

The signal provided by the integrator 150 is provided via a connection 155 for further processing. In addition, a microcomputer 165 may be connected to the control inputs of the controllable amplifiers 115, 120. The microcomputer 165 compares the provided signal with a threshold value and outputs at an output 170 a signal which indicates the metallic object. The signal can be presented to a user of the metal detector 105 visibly and/or audibly.

Furthermore, the microcomputer 165 can perform further processing of the signals tapped off from the control inputs of the controllable amplifiers 115, 120 and can take said signals as a basis for controlling parameters of the measuring apparatus 100. By way of example, a frequency or signal shape of the alternating voltages at the outputs of the clock generator 110 can be varied or a sensitivity of the reception amplifier 140 can be changed. In a further embodiment, further instances of the elements shown from the measuring apparatus 100 are implemented by the microcomputer 165, for example the clock generator 110, the synchronous demodulator 145 or the integrator 150.

The same signal from the integrator 150 is also used to control the gain factors of the controllable amplifiers 115 and 120, wherein the second controllable amplifier 120 is connected directly to the output of the integrator 150 and the first controllable amplifier 115 is connected to the output of the integrator 150 by means of an inverter 160. The inverter 160 prompts inversion of the signal with which it is provided such that on the basis of the output signal from the integrator 150 the gain factor of the first controllable amplifier 115 increases to the extent that the gain factor of the second controllable amplifier 120 decreases, or vice versa. It is also conceivable for only the gain factor of one of the two controllable amplifiers 115, 120 to be controlled, while the gain factor of the second controllable amplifier 115, 120 is kept at a fixed value.

In comparison with a measuring apparatus having only one transmission coil, a temperature influence on the impedance of the transmission coils 125, 130 is compensated for by appropriate changes in both transmission coils 125, 130 in the case of the present measuring apparatus. Furthermore, a suitable geometric arrangement of the transmission coils 125, 130 allows an increased directional effect of the measuring apparatus 100 to be attained.

Figure 2:
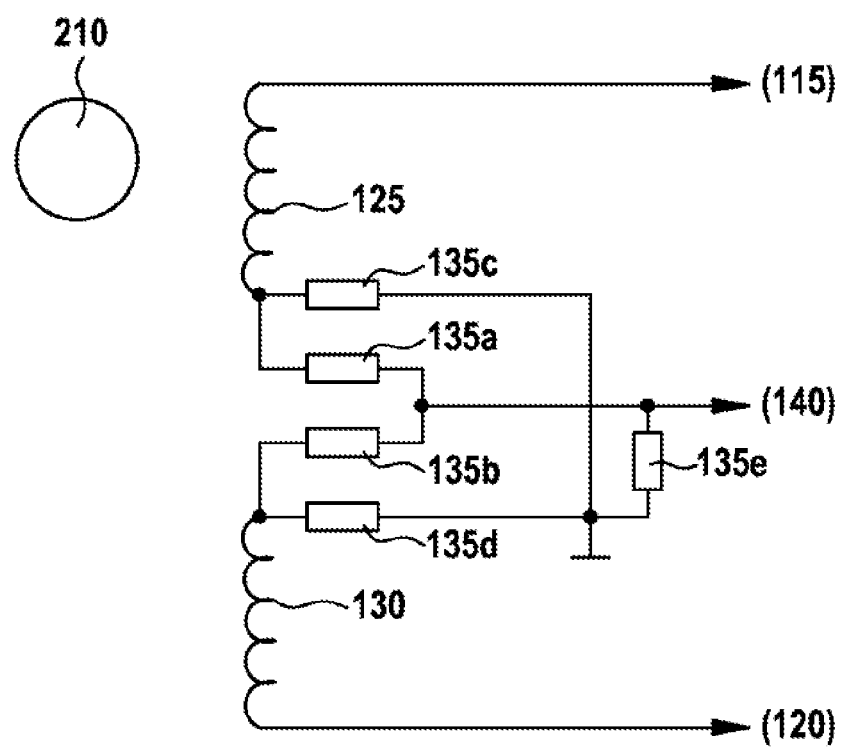
FIG. 2 shows an arrangement of coils and a metallic object on the measuring apparatus from FIG. 1.

FIG. 2 shows an arrangement 200 of the transmission coils 125, 130 relative to a metallic object 210 in order to explain the measurement principle of the measuring apparatus 100 from FIG. 1. The transmission coils 125 and 130 are oriented relative to one another such that the directions of their main magnetic fields are in alignment with one another, with the transmission coils 125, 130 being at a certain distance. In the case of transmission coils 125, 130 which have a diameter substantially greater than their length, for example when the transmission coils 125, 130 are in the form of printed coils, the transmission coils 125, 130 may be situated in mutually parallel planes, for example on opposite surfaces of a circuit board in the example of the printed coils.

As described above with reference to FIG. 1, the transmission coils 125, 130 are arranged and connected to one another such that they each generate alternating magnetic fields on the basis of the signals provided by the clock generator 110.

A metallic object 210 is situated in the region of the magnetic fields from the transmission coils 125 and 130, said metallic object 210 being at a shorter distance from the first transmission coil 125 than from the second transmission coil 130. The magnetic field from the first transmission coil 125 is thus influenced by the metallic object 210 to a greater extent than the magnetic field from the second transmission coil 130. Accordingly, the impedance of the first transmission coil 125 differs from the impedance of the second transmission coil 130. If the impedances of the transmission coils 125 and 130 are of different magnitude, the voltage between the resistors 135*a* and 135*b* has an AC voltage component that is different than zero and that is in sync with the alternating voltages of the controllable amplifiers 115, 120. This synchronous AC voltage component is determined by the synchronous demodulator 145 and the downstream integrator 150. The absolute value of the synchronous AC voltage component of the differential voltage is dependent on the imbalance in the impedances of the transmission coils 125, 130. The output of the integrator 150 therefore produces a signal which is dependent on the imbalance in the magnetic fields. The phase of the synchronous AC voltage component of the differential voltage differs by 180° depending on whether the metallic object 210 is closer to the first transmission coil 125 than to the second transmission coil 130, as shown, or whether the metallic object 210 is closer to the second transmission coil 130 than to the first transmission coil 125.

Depending on the output voltage from the integrator 150, the gain factors of the controllable amplifiers 115, 120 are altered in different directions, with the result that the transmission coils 125, 130 are supplied with voltages of different magnitude. It is also possible for only the gain factor of one of the controllable amplifiers 125, 130 to be altered, while the gain factor of the second controllable amplifier 125, 130 is kept at a fixed value. For the arrangement shown in FIG. 1, each of the two transmission coils 125, 130 carries the same current at any time. On account of the different impedances of the transmission coils 125, 130 when an object 220 is present, however, the voltage drop across the transmission coils 125 and 130 is of different magnitude and a synchronous AC voltage component of the differential voltage that is different than zero is obtained.

The presence of the metallic object 210 in the magnetic fields can be sensed by virtue of the deviation in the control signal applied to the connection 155 from zero. In one embodiment, metallic objects are sensed only on the basis of a predetermined arithmetic sign of the control signal. Thus, objects on one side of the transmission coils 125, 130 are ignored, these possibly being caused by a user of the measuring apparatus, for example.

In a further embodiment shown in FIG. 2, a third resistor 135*c* and a fourth resistor 135*d* are provided, each of which route a connection of the transmission coils 125, 130 which is connected to one of the resistors 135*a* and 135*b* to ground. A fifth resistor 135*e* is routed from the input of the input amplifier 140 to ground. In contrast with the embodiment shown in FIG. 1, the embodiment shown in FIG. 2 allows each of the two transmission coils to carry different currents at any time. The ground-referenced polarities and amplitudes of the alternating voltages applied to the two transmission coils 125, 130 therefore have a separate influence on each of the two magnetic fields produced in the coils 125, 130. The following variations of the measuring apparatus 100 can thus be implemented:

- the controllable amplifiers 115 and 120 deliver opposite voltages, referenced to ground. In the object-free case, the voltages have identical amplitudes. In the presence of a metallic object 210, the amplitudes of the applied voltages differ. Preferably, magnetic fields in the same direction are used, but magnetic fields in opposite directions are also conceivable.
- the controllable amplifiers 115 and 120 deliver voltages in the same direction, referenced to ground, and the windings of the transmission coils 125, 130 are in the same sense, with the result that magnetic fields in the same direction are produced. In this case, the voltages which are applied to the two transmission coils 125, 130 during one half-cycle already have different amplitudes in the object-free case. However, in the subsequent half-cycle, these amplitudes appear on the respective other transmission coil 125, 130 in the object-free case. In the presence of a metallic object 210, on the other hand, the amplitudes on the respective other transmission coil 125, 130 also differ in successive half-cycles.
- the controllable amplifiers 115 and 120 deliver voltages in the same direction, referenced to ground, and the windings of the transmission coils 125, 130 are in opposite senses, with the result that magnetic fields in opposite directions are produced. For the amplitudes of the voltages, the comments regarding the preceding variation apply.

Figure 3:
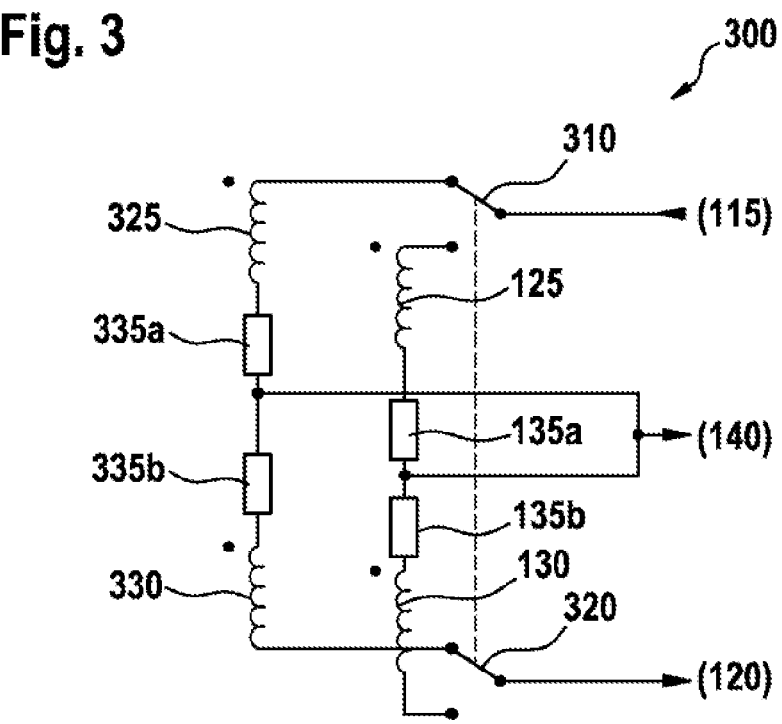
FIG. 3 shows an arrangement of a plurality of pairs of transmission coils for the measuring apparatus from FIG. 1.

FIG. 3 shows an arrangement 300 with a plurality of pairs of transmission coils for the measuring apparatus 100 from FIG. 1. In addition to the arrangement of the transmission coils 125, 130 with the resistors 135a, 135b which is described with reference to FIG. 1, appropriately connected further transmission coils 325, 330 with further resistors 335a, 335b are provided. Two switches 310 and 320 that are coupled to one another connect respective connections of the transmission coils 125, 130 or of the transmission coils 325, 330 selectively to the outputs of the controllable amplifiers 115, 120 from FIG. 1. The connections between mutually corresponding resistors 135a, 135b, 335a and 335b are connected to one another and are routed to the input amplifier 140.

The coil pairs 125, 130 and 325, 330 may be arranged in one plane or may be situated in different planes. Particularly coils that are situated next to one another may be in the form of printed coils. If the differential voltage on the input amplifier 140 changes when the switches 115 and 120 are changed over, it is possible to infer a direction in which the metallic object 210 is situated on the basis of the geometric arrangement of the coil pairs 125, 130 and 325, 330, for example by means of triangulation. Similarly, it is possible to infer a distance of the object. The direction-finding can be refined by further coil pairs. If a large number of sufficiently closely arranged transmission coils are used, it is possible to increase a resolution of the measuring apparatus 100 until it enters a graphical range.

Figure 4:
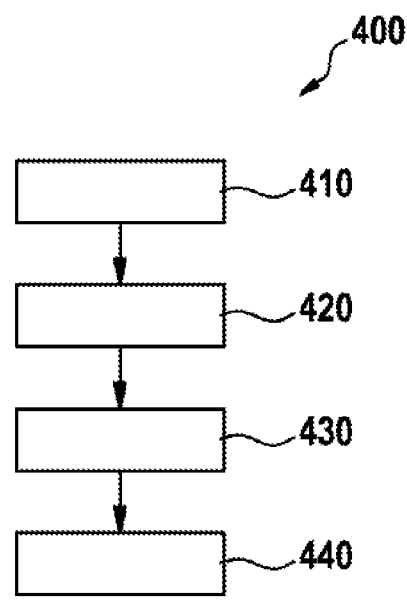
FIG. 4 shows a flowchart for a method for the measuring device from FIG. 1.

FIG. 4 shows a schematic flowchart of a method 400 for sensing a metallic object 210 in line with the measuring apparatus 100 from FIGS. 1 and 2. In a step 410, the transmission coils 125, 130 are used to produce magnetic alternating fields oriented in the same direction. In a subsequent step 420, the transmission coils 125, 130 are supplied with phase shifted alternating voltages from the clock generator 110 by controlling the gain factors of the amplifiers 115, 120, specifically such that the AC voltage component of the differential voltage—which component is in sync with the alternating voltages—is minimized in terms of absolute value. In a final step 430, the metallic object 210 is sensed when the ratio of the alternating voltages does not correspond to the ratio of the currents flowing through the transmission coils 125, 130.

In the measuring apparatus shown in FIG. 1, the currents through the two transmission coils 125, 130 are always the same, and the ratio of the currents is therefore 1. The differential voltage at the input of the input amplifier 140, to be more precise the synchronous AC voltage component of the differential voltage, is regulated to zero by using the controllable amplifiers 115, 120 to apply different voltages to the two transmission coils 125, 130. In this case, the ratio of the voltages across the transmission coils 125, 130 differs from 1, and hence from the ratio of the currents through the transmission coils 125, 130. The ratio of the voltages corresponds to the control signal at the output of the integrator 150. The control signal at the connection 155 is thus not equal to zero precisely when the ratio of the voltages across the transmission coils 125, 130 is not equal to 1, which is caused by different impedances of the transmission coils 125 and 130. If the impedances of the transmission coils 125, 130 are the same in the object-free case, the signal applied to the connection 155 indicates the object 210 if the signal is not equal to zero.

The invention claimed is:

1. A measuring apparatus for sensing a metallic object comprising:
    two transmission coils connected in series with on another configured to produce overlaid magnetic fields; and
    a control circuit having two outputs and an input, the two outputs being operably connected to each of the transmission coils and the input being operably connected to a differential voltage at a point between the transmission coils, the control circuit being configured to:
    receive the differential voltage at the input;
    supply the transmission coils with alternating voltages via the two outputs to produce the overlaid magnetic fields, the alternating voltages being such that an absolute value of an AC voltage component of the differential voltage is minimized, the AC voltage component being in sync with the alternating voltages; and
    sense the metallic object when a ratio of the alternating voltages does not correspond to a ratio of impedances of the transmission coils in an absence of the metallic object in the overlaid magnetic fields.

2. The measuring apparatus as claimed in claim 1, wherein the alternating voltages are AC voltages having a phase shift relative to one another to change the magnetic fields of the transmission coils periodically in terms of absolute value and phase.

3. The measuring apparatus as claimed in claim 1, wherein each of the transmission coils includes a series-connected non-reactive resistor which is part of a complex resistance of each of the transmission coils.

4. The measuring apparatus as claimed in claim 1 wherein a respective connection of each transmission coil is connected to ground by a resistor.

5. The measuring apparatus as claimed in claim 1, wherein the transmission coils are arranged in two spaced, parallel planes, such that the magnetic fields are oriented parallel.

6. The measuring apparatus as claimed in claim 1, wherein at least one of the transmission coils is an air-core coil.

7. The measuring apparatus as claimed in claim 6, wherein the air-core coil is a printed circuit on a circuit board.

8. A method for sensing a metallic object, comprising:
    producing overlaid magnetic fields with two transmission coils connected in series with on another;
    determining a differential voltage at a point between the transmission coils;
    supplying the transmission coils with alternating voltages such that an absolute value of an AC voltage component of the differential voltage is minimized, the AC voltage component being in sync with the alternating voltages; and
    sensing the metallic object when a ratio of the alternating voltages does not correspond to a ratio of impedances of the transmission coils in an absence of the metallic object in the overlaid magnetic fields.

9. A non-transitory computer program product having program code for carrying out a method when said computer program product is executed on a processing device or is stored on a computer-readable data storage medium, the method comprising:
    producing overlaid magnetic fields with two transmission coils connected in series with on another;
    determining a differential voltage at a point between the transmission coils;
    supplying the transmission coils with alternating voltages such that an absolute value of an AC voltage component of the differential voltage is minimized, the AC voltage component being in sync with the alternating voltages; and
    sensing a metallic object when a ratio of the alternating voltage does not correspond to a ratio of impedance of the transmission coils in an absence of the metallic object in overlaid the magnetic fields.

10. The measuring apparatus as claimed in claim 1, wherein impedances of both of the two transmission coils are influenced by a presence of the metallic object in the overlaid magnetic fields.

* * * * *